United States Patent [19]

Shihata

[11] 4,295,464
[45] Oct. 20, 1981

[54] URETERIC STONE EXTRACTOR WITH TWO BALLOONED CATHETERS

[76] Inventor: Alfred A. Shihata, 3584 Fairlanes Ave., SW., Grandville, Mich. 49418

[21] Appl. No.: 131,937

[22] Filed: Mar. 21, 1980

[51] Int. Cl.³ .................. A61B 19/00; A61B 17/00; A61M 25/00; A61M 29/02
[52] U.S. Cl. .................................. 128/1 R; 128/328; 128/349 B; 128/349 BV; 128/344
[58] Field of Search ............... 128/328, 349 R, 349 B, 128/349 BV, 344, 325, 1 R

[56] References Cited

U.S. PATENT DOCUMENTS

| 3,827,437 | 8/1974 | Inaba | 128/328 |
| 4,148,319 | 4/1979 | Kasper et al. | 128/349 B |
| 4,198,981 | 4/1980 | Sinnreich | 128/344 |
| 4,202,346 | 5/1980 | Granier | 128/349 B |
| 4,243,040 | 1/1981 | Beecher | 128/349 B |

OTHER PUBLICATIONS

"Some New Concepts of Stones of Uretal Stones," *Progressive Surg.*, vol. 13, pp. 185-205, Karger, Basel, 1974.
"Cystoscopic Rx of Stones in the Ureter with Spec. Reference to Lg. Calculi, Based on 1550 Cases", Dourmashkin, R. L., pub. & date unknown.
"A Double-Balloon Ureteric Stone Extractor", *The Lancet*, Oct. 4, 1969, pp. 724, 725.
Advertisement of V. Mueller Div. of American Hosp. Supply Corp., pp. 400-401, pub. & date unknown.

*Primary Examiner*—Robert W. Michell
*Assistant Examiner*—C. W. Shedd
*Attorney, Agent, or Firm*—John E. McGarry

[57] ABSTRACT

A ureteric stone extractor (100) is disclosed wherein an inner dislodger catheter (101) is slidable within a relatively larger outer dialator catheter (102). The dislodger catheter (101) comprises a lumen (104) having a stiffening metal stylet (106) therein to allow it to easily pass beyond a stone arrested within a ureter. A dislodger balloon (107) is eccentrically attached to the inner catheter (101) and can be inflated once the inner catheter (101) is positioned above and beyond the arrested stone. Nylon strings (110) positioned along longitudinal axes of the dislodger balloon (107) are manipulable by an attending physician to ensure that the dislodger catheter (101) and the strings (110) entrap the stone and to apply a downward force by the dislodger balloon (107) to the stone sufficient to dislodge it from the ureteral walls. The outer dilator catheter (102) has a cylindrical dilator balloon (113) attached thereto to effect distension and dilation of the ureter below the arrested stone, thereby providing a sufficient spacial area into which the stone can be moved.

17 Claims, 6 Drawing Figures

URETERIC STONE EXTRACTOR WITH TWO BALLOONED CATHETERS

BACKGROUND OF THE INVENTION

1. Technical Field

This invention relates to medical treatment of stones arrested within a ureter, and more specifically, relates to catheter apparatus and methods for extracting ureteric stones without necessitating major surgery.

2. State of the Prior Art

For many years, individuals have been medically plagued by stones normally formed in renal calyces or the pelvis which pass to and are arrested within the ureter. Among other medical problems, these stones often cause blockage of urine produced by the kidneys with resultant ureteral colic and accompanying severe pain. It has long been recognized advantageous to treat patients having ureteric stones using procedures which do not require major open surgery involving incisions of the ureter. The dangers and complications associated with such surgery are well-known to any physician. Further, certain patients have medical histories prohibiting major surgery involving the ureteral area.

One early treatment procedure for ureteral stones was based on the concept that spasm in the smooth muscle of the ureteral wall prevented passage of the stone and passage of urine around the stone. Accordingly, the procedure involved use of spasmolytic drugs. However, it has been shown in various studies that spasm of the ureteral wall is not an overriding factor in the arrestment of ureteral stones. Therefore, spasmolytic drugs are not substantially effective.

Other early treatment procedures were based on the simple mechanical principle that a stone is arrested in the ureter when the force which is driving downward on the stone is smaller than the frictional force occurring between the stone and the ureteral wall. Historically, it was therefore thought that any treatment method which increased the downward driving force on the stone would be valuable to accomplish stone passage. Accordingly, patients were urged to increase fluid intake, thereby increasing the volume and resultant pressure of urine produced by the kidneys which was blocked above the stone. However, studies have shown that sudden pressure increase above the ureteral stone caused by discharge of urine from the kidneys actually causes an increased magnitude of frictional force between the stone and the ureteral wall. Therefore, passage of the ureteral stone is not facilitated by the increased urine, and further, severity of ureteral colic is actually increased.

The treatment procedures which merely attempt to increase the magnitude of downward forces above the arrested stone do not take into consideration the mechanical principles of frictional forces or the interrelationships of these principles to the physiological composition of the ureter. The frictional force at a point of contact between surfaces of the stone and the ureteral wall is equivalent to the product of a coefficient of friction and the force pressing between the stone and wall perpendicular to the plane of contact of the surfaces. A coefficient of friction for any two particular surfaces is dependent only on the materials involved and the "condition" of the surfaces.

As now understood in the physiological arts, the magnitude of the aforementioned perpendicular force between the stone and the ureteral wall is dependent upon several factors. These factors comprise: stone size, ureter width, and distensibility of the ureteral wall. Regarding stone size, the tensional force of the ureteral wall at the location of arrestment of the ureteral stone increases with respect to the diameter of the stone. As a general rule, stones having a diameter smaller than 2 millimeters pass through the ureter without causing substantial difficulty. Stones having a diameter greater than 2 millimeters but less than 4 millimeters also usually pass through the ureter but can cause associated ureteral colic. Various studies have shown that stones having a diameter of 4 to 6 millimeters independently pass through the ureter at a rate of approximately 50%. Stones having a diameter greater than 6 millimeters seldom pass through the ureter without medical treatment.

As known in the medical arts, the ureter comprises three sections of relatively narrow width. Frictional force between the stone and the ureter of course becomes greater at these narrow sections. Accordingly, it is at these sections that stones are often arrested. The relatively narrow sections are commonly known as the pyelo-ureteral conjunction, the passage over the crossing of iliac vessels and the uretro vesical junction which is the distal portion of the ureter.

Frictional forces between an object and a tubular structure surrounding the object increase inversely with the distensibility of the tubular structure. The distensibility of the ureteral walls is dependent on the individual distensibilities and arrangement of the materials composing the walls. The ureteral walls comprise approximately 70% fibrous collagen tissue having a distensibility substantially equivalent to 0.01% of the distensibility of smooth muscle fiber which substantially comprises the remainder of the ureteral wall composition. Accordingly, it is the collagen tissue that is determinative of the distensibility of the ureter and corresponding frictional force between a stone and the ureteral walls. Further, a moderate distension of the ureteral walls in the upper and middle portions of the ureter causes the collagen fibers to become contentrically arranged around the ureter lumen. Collagen fibers are always concentrically arranged in the lower portion of the lumen. This concentric arrangement offers substantial resistance to distension of the ureteral walls and, accordingly, produces large frictional forces in response to attempted distension.

With knowledge of the densities and arrangement of the collagen and muscle fibers in the ureter, it is surprising that relatively large stones will sometimes independently pass through the ureter. This phenomenon can be explained in view of the "visco-elastic" behavior of living tissue. In accordance with general mechanical principles, when a force is applied upon an elastic body, the deformation of the body is proportional to the magnitude of the force. This principle is commonly known as "Hooke's Law." The deformation of a visco-elastic material depends not only on the magnitude of the force applied to the material, but also upon the duration of the applied force. All living tissue, including collagen tissue, has visco-elastic properties. If a constant force is applied to such visco-elastic material, the material continuously "stretches" until it reaches an equilibrium state. This stretching and adjustment to equilibrium is commonly known as "creep." Further, if visco-elastic living tissue is stretched and then maintained at its new position for a substantial period of time, the tensional force generated by the living tissue will fall to a steady-state value. This particular principal is commonly known as "stress relaxation."

The aforementioned principles of creep and stress relaxation can readily be applied to arrestment of stones within a ureter. As a stone passes into the ureteral area, there is a distension of the ureteral walls which produces substantially large resistance and resultant frictional forces with the stone. Accordingly, the stone is arrested within the ureter. If the stone has been arrested at a particular position on the ureteral wall for a substantial period of time, the tensional force of the ureteral wall gradually ceases in accordance with the principle of stress relaxation. Accordingly, the frictional force between the stone and the ureteral wall will decrease and a stone can often pass from its arrested position towards the bladder.

However, other physiological phenomenon also occur when a ureteral wall is continuously deformed at a position of arrestment of a stone. As known in the medical art, a horizontal "bar" of the ureteral wall materials will often be formed below the stone, effectively blocking its passage. The size of this horizontal bar depends on the magnitude and duration of the driving force of the stone. It is this bar which often occurs when the pressure of urine above the stone increases.

Several types of devices exist in the prior art which are designed to extract ureteric stones without necessity of major open surgery. However, each of these devices suffers from limitations not found in the present invention and does not take into consideration all of the mechanical and physiological principles previously discussed herein. Further, substantially all of these devices are limited to extractions of ureteral stones in the lower one-third of the ureter with limited success to extract any stones above the lower third section. Additionally, these devices can produce varying degrees of trauma to the ureter and are therefor somewhat dangerous.

One such prior art device is commonly known as the Dormia ureteral stone dislodger. This device, and devices having limited modifications thereof, are utilized in a large percentage of medical centers now performing ureteral stone extraction. The basic Dormia stone dislodger comprises a catheter having a retractable spring wire mechanism. The spring wire mechanism is operable to activate a four wire pear-shaped basket having an opening therein to entrap a ureteral stone. The Dormia stone dislodger, like other prior art devices, is limited to extraction of ureteral stones in the lower third section of the ureter. Further, this dislodger is substantially limited in usefulness to extract stones having a diameter smaller than 8 millimeters.

Several other limitations of the Dormia stone dislodger also exist. The structure of the basket and the materials of which it is compressed can cause entrapment of the basket within the ureter and/or possible perforation of the ureteral wall. Additionally, the lack of expansive power of the wires of the pear-shaped basket to fully dilate the ureter has caused a substantially high failure rate when attempting stone extraction.

Another prior art device comprises a single catheter with two inflatable balloons located at concentric predetermined positions near the tip of the catheter. A syringe plunger attached to the lower end of the catheter provides variation in balloon size while the catheter is positioned in the ureter. The catheter is manipulated so that the arrested stone is between the balloons and is then slowly withdrawn with the lower balloon acting as a dilator and the upper balloon pushing the stone toward the bladder. With only a single catheter, this device does not allow the balloons to be separately manipulated. Further, the fixed positional relationship of the balloons and the concentric attachment of the upper balloon to the catheter limits the adaptability of the device to achieve extraction of relatively large stones, and, more particularly, the extraction of any size arrested above the lower third ureter section.

SUMMARY OF THE INVENTION

Advantageously, a technical advance is achieved in a ureteric stone extractor capable of extracting ureteral stones arrested above the lower one-third section of a ureter and further capable of extracting stones having a diameter greater than 8 millimeters. The stone extractor comprises structure and materials adapted to substantially minimize failure of accomplishment of stone extraction and complications which can arise therefrom.

The extractor comprises a first catheter means for positioning a first inflatable means below the position of arrestment of the ureteral stone. A second catheter means is adapted to apply a downward force to the ureteral stone sufficient to achieve dislodgement of the stone from the inner walls of the ureter. The first inflatable means applies an outward radial force to the ureter inner walls to distend the same in response to the force in a manner such that a stress relaxation state is achieved. The second catheter means is manually manipulable to move the ureteral stone into the ureteric area distended by the first inflatable means.

The second catheter means is connected to a second inflatable means which is positionable above the position of arrestment of the ureteral stone for dislodging the ureteral stone from the ureter inner walls. The second inflatable means is movable relative to the first inflatable means and is eccentrically arranged about the second catheter means. The second catheter means comprises a dislodger catheter connected to the second inflatable means for manually extending the second inflatable means to the position above the ureteral stone. The first catheter means comprises a dilator catheter extendible into the ureter and connected to the first inflatable means for positioning the first inflatable means below the ureteral stone. Additionally, the dislodger catheter means is extendible through and beyond the dilator catheter means.

The first inflatable means comprises a dilator balloon having a cylindrical shape and arranged concentrically about a first lumen of the dilator catheter and inflatable by injection of material through openings of first lumen. The second inflatable means comprises a dislodger balloon connected to the dislodger catheter and arranged eccentrically about a lumen of the dislodger catheter. The dislodger balloon is inflatable by injection of material through openings of the dislodger lumen.

A method for achieving stone extraction in accordance with the invention comprises the application of a gradually increasing outward radial force to the inner walls of the ureter immediately below the position of the arrested stone. This increasing radial force is sufficient to induce stress relaxation of the inner walls to the extent that the diameter of the spacial area between the walls at the position of concentric force application is larger than the maximum diameter of the stone. The application of the concentric force is then ceased and a downward force is applied from a position above the stone sufficient to dislodge the stone from the inner walls. The stone is then manipulated into the spacial area already dilated by application of the radial force. The aforementioned procedure is repeated until the stone passes into the bladder area of the patient.

BRIEF DESCRIPTION OF DRAWINGS

The invention will now be described with reference to the drawings in which.

DETAILED DESCRIPTION

Figure 3:
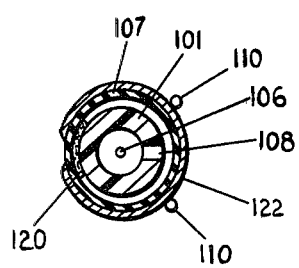
FIG. 3 depicts a cross-sectional top view of the ureteric stone extractor shown in FIG. 1 taken along the axis 3—3 of FIG. 1.

The invention will now be described with reference to the drawings and to FIGS. 1, 3 and 4 in particular. The principles of this invention are disclosed, by way of example, in a ureteric stone extractor 100. A stone extractor of this type can be utilized for removing ureteral stones without necessitating major open surgery on the patient. As will be described herein, extractor 100 is adapted to apply a downward force above the position of ureteral stone arrestment and correspondingly decrease the frictional attraction between the stone and ureteral inner walls by dilating the ureter sufficiently to induce a stress relaxation state.

Figure 1:
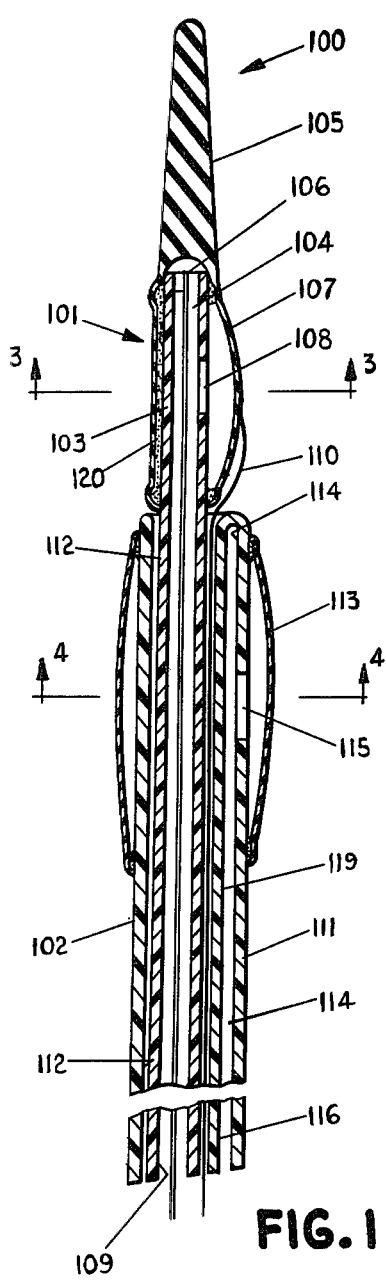
FIG. 1 depicts a sectional view of one illustrative embodiment of a ureteric stone extractor in accordance with the invention.

Extractor 100 comprises an inner dislodger catheter 101 and an outer dilator catheter 102 as shown in FIG. 1. Dislodger catheter 101 is depicted in FIG. 1 extending through and in part beyond dilator catheter 102. Catheter 101 can be manually extended into a patient's ureter and beyond the dilator catheter 102 and provides a means for positioning subsequently described apparatus above the arrested stone. Dislodger catheter 101 comprises tubular walls 103 within a cylindrical lumen 104 formed therein. Catheter 101 terminates at its far end in a conical tapering structure 105 comprising a filiform tip, flexible but having, for example, a spring wire inner core or the like to provide sufficient rigidity for insertion into the ureter. Preferably, the size of the dislodger catheter 101 can comprise a diameter at its maximum width of approximately 3 to 4 F. (F is a standard unit of measure for catheters commonly known and used in the medical arts and is approximately equal to 0.33 millimeters).

Within the lumen 104 of dislodger catheter 101 is a metal stylet 106 which provides a stiffening effect necessary to allow the end of catheter 101 to easily pass beyond a stone arrested within the ureter.

Connected to dislodger catheter 101 is an eccentric balloon 107 which is attached to the exterior of tubular walls 103 near the top of lumen 104 through a suitable adhesive 120. Dislodger balloon 107 is depicted in FIG. 1 in a deflated state and provides an inflatable means for applying, at a requisite time as subsequently described herein, a downward force sufficient to dislodge the arrested stone. Additionally, when balloon 107 is in an inflated state, migration of the dislodged stone toward the kidneys is prohibited. As shown in subsequently described figures of the drawing herein, dislodger balloon 107 is eccentric with respect to the tubular structure of dislodger catheter 101 to enable the balloon to be positioned immediately above the stone during the extraction process.

The dislodger balloon 107 is connected to the tubular walls 103 of dislodger catheter 101 in a manner and position such that an opening 108 in the tubular walls 103 from lumen 104 is interior to balloon 107. An additional opening 109 of lumen 104 exists at the lower end of stone extractor 100. Opening 109 remains external to the patient's ureter during all phases of the extraction process. A suitable syringe or other means (not shown) can be utilized to inject a material into lumen 104 to inflate the dislodger balloon 107 to a requisite size after positioning thereof. As evident to any physician having knowledge of the invention, a radio-opaque inflation material can be advantageously utilized to provide visualization by the physician via X-ray type machines commonly known in the medical art. When the eccentric dislodger balloon 107 is inflated to a requisite size, a stopcock or other suitable means can be utilized to close the lumen opening 109. Dislodger 107 can be of any suitable volumetric capacity, preferably such as approximately 2 cubic centimeters (cc).

Attached to and passing longitudinally around the eccentric dislodger balloon 107 are a pair of strings 110, one of which is shown in FIG. 1. Strings 110 provide a means for manually manipulating dislodger balloon 107 to achieve dislodgement of the arrested stone and to move it downward into an area of the ureter dilated in a manner subsequently described herein. Further, the strings allow the application of pressure to maintain balloon 107 in a correct spacial position. Strings 110 are preferably composed of nylon material or the like, and are attached to dislodger balloon 107 at suitable positions subsequently described herein. The strings are preferably further attached to the base of filiform tip 105 to provide greater stability. Strings 110 pass from the dislodger balloon 107 to the external area of the patient's ureter along the exterior of tubular walls 103 of dislodger catheter 101. These strings are accessible to the physician and utilized for manipulation of eccentric balloon 107 during the stone extraction process.

Figure 4:
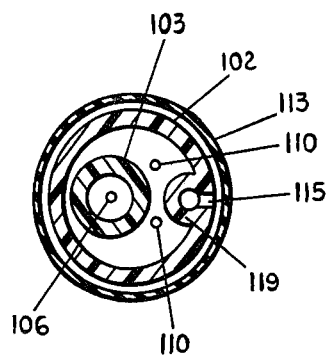
FIG. 4 depicts a cross-sectional top view of the ureteric stone extractor shown in FIG. 1 taken along axis 4—4 of FIG. 1.
Figure 6:
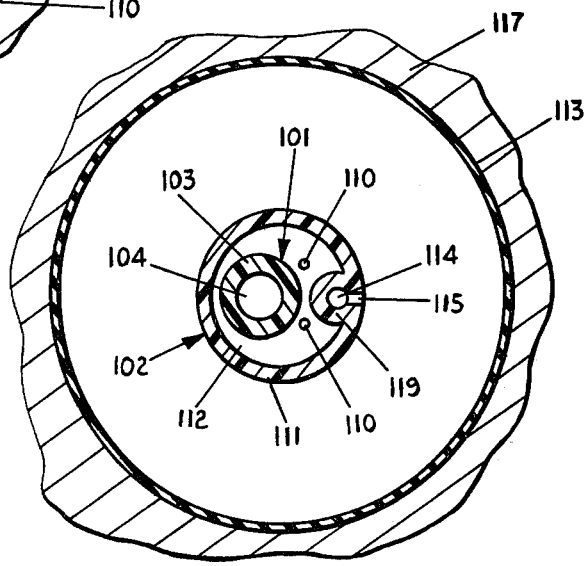
FIG. 6 depicts a cross-sectional top view of the ureteric stone extractor shown in FIG. 2 taken along axis 6—6 of FIG. 2.

Surrounding the dislodger catheter 101 is the relatively larger outer dilator catheter 102 as shown in FIGS. 1, 4 and 6. Dilator catheter 102 provides an extendable means for positioning subsequently described inflatable means below the arrested stone and gradually dilating the ureter through the use thereof. Catheter 102 comprises a cylindrical structure having substantially tubular walls 111 which form an open-ended first lumen 112 therein. The dilator catheter 102 is of a requisite size to allow the dislodger catheter 101 to be slidably received within first lumen 112 and extendable beyond its open upper end. This extension capability allows the previously described dislodger balloon 107 to be passed beyond and come in contact with the upper portion of the ureter above the stone for purposes of applying a downward dislodging force. Preferably, catheter 102 can have a maximum width diameter of approximately 7 to 8 F, which is sufficiently small to readily allow insertion thereof into the ureter.

Connected to the upper portion of dilator catheter 102 is a dilator balloon 113 cylindrical in shape and arranged concentrically around the exterior tubular walls 111. Dilator balloon 113 is depicted in a deflated state in FIG. 1 similar to dislodger balloon 107. As subsequently described herein, balloon 113 provides an inflatable means for applying a gradually increasing outward radial force to the inner walls of the ureter immediately below the arrested stone, thereby distending the ureteral walls and dilating the spacial area therebetween.

Catheter 102 further comprises a second cylindrically shaped lumen 114 relatively smaller than first lumen 112 and formed by wall 119. Lumen 114 is closed at its upper portion and comprises an opening 115 through tubular walls 111. The dilator balloon 113 is connected to catheter 102 in a manner and position such that opening 115 is interior to balloon 113. An additional opening 116 to lumen 114 exists at the lower end of catheter 102 and remains external to the ureter during the extraction process. In a manner similar to that previously described with respect to dislodger balloon 107, the attending physician can utilize a syringe or other suitable means to inject a radio-opaque material into lumen 114 through opening 116, thereby inflating dilator balloon 113 via opening 115. When dilator balloon 113 is inflated to its requisite size, a stopcock or other suitable means can be utilized to close opening 116.

Dilator balloon 113 can be of any suitable volumetric capacity, preferably, a capacity of approximately 10 cc. Catheters 101 and 102 can be composed of any materials generally known in the arts which are suitable for insertion into human organs. For example, the catheters can comprise Teflon or like material. Further, the previously described dislodger balloon 107 can be reinforced with Latex rubber layers 122 or other suitable materials at positions where strings 110 attach and pull on the balloon 107, and above the area in contact with the arrested stone.

Figure 2:
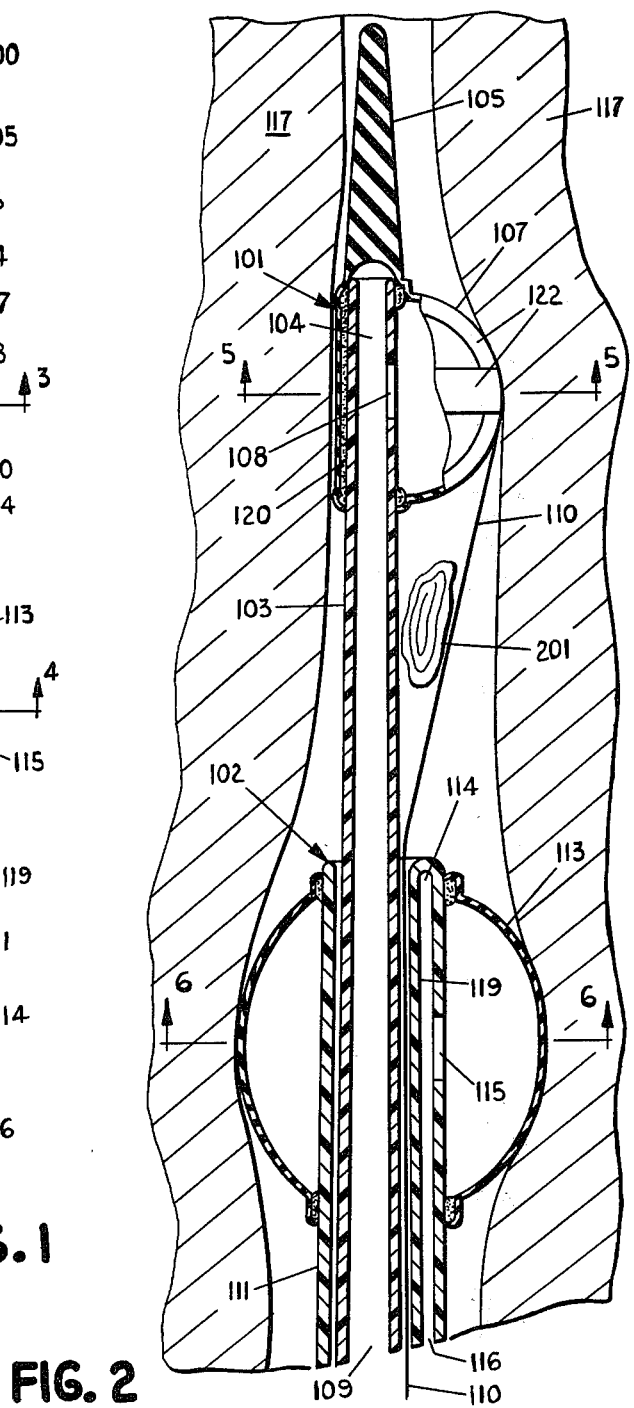
FIG. 2 is a sectional view of the ureteric stone extractor shown in FIG. 1 in a ureter with the balloon elements of the extractor in an inflated position with the metal stylet removed.
Figure 5:
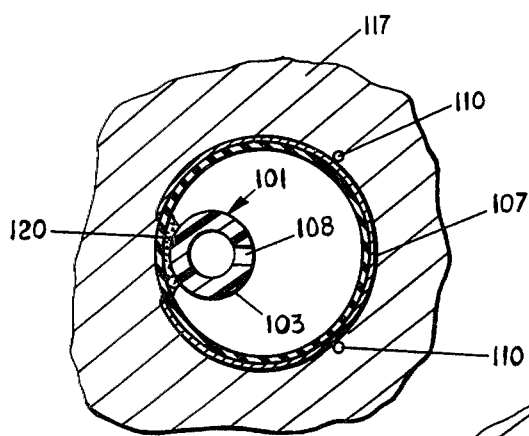
FIG. 5 depicts a cross-sectional top view of the ureteric stone extractor shown in FIG. 2 taken along axis 5—5 of FIG. 2.

Reference is now made to FIGS. 2, 5 and 6 for a description of the operation of the invention. The dislodger balloon 107 and dilator balloon 113 are both in an inflated state. It should be noted that FIG. 2 does not depict the metal stylet 106 which is removed by the physician once the extractor 100 is in suitable position within the patient's ureter.

Before the extraction process begins, the patient is normally put under a general anesthesia in a lithotomy position, which is a position commonly known in the medical art and utilized when a physician makes a cystoscopic examination to extract a stone by manipulation. Commonly known X-ray apparatus and an image intensifier screen are utilized throughout the extraction procedure to provide visual location of the stone and to further provide visual indications of the relative positions of the previously described catheters and balloons with respect to the stone. Preferably, the ureteric orifice is initially catheterized for purposes of gently injecting a sterile mineral oil or like substance in the ureter where the stone is arrested. The injected mineral oil provides additional lubrication for purposes of decreasing the friction between the arrested stone and the ureteral walls, thereby aiding the extraction process.

By means such as a suitable linear panendoscope (e.g. a McCarthy's foroblique cystoscope well known in the medical arts), the ureteric stone extractor 100 is introduced into the ureter through the ureteric orifice. Extractor 100 is passed up through the ureter while visualized by the physician on the image intensifier screen. FIGS. 2, 5 and 6 depict extractor 100 within the area between ureteral walls 117. At the time extractor 100 is in a suitable position with respect to the arrested stone, dislodger catheter 101 is extended through and beyond the dilator catheter 102. It can be somewhat useful to the extraction process if the extension of dislodger catheter 101 causes partial dislodgement of the arrested stone and slight movement towards the upper portion of the ureter and the kidney. This action is useful since the portion of the ureter above the arrested stone is normally somewhat dilated and provides a larger spacial area for subsequent manipulation.

The dislodger catheter 101 is extended until it appears to the physician that the presently delfated dislodger balloon 107 is positioned above the stone. When the physician is certain of correct positioning, metal stylet 106 is removed from lumen 104 of catheter 101. It should be noted that FIG. 2 does not depict stylet 106 since removal occurs prior to inflation of balloons 107 and 113. Dislodger balloon 107 is then inflated with radio-opaque material in a manner previously described with respect to FIG. 1. Balloon 107 is inflated sufficiently to prohibit possible extensive migration of the stone 201 towards the kidneys if it becomes completely dislodged. FIG. 2 depicts the dislodger balloon 107 in an inflated state above a stone 201 to be extracted.

Dilator catheter 102 is then positioned such that dilator balloon 113 is immediately below stone 201. Balloon 113 is then also inflated with radio-opaque material in the manner described with respect to FIG. 1. The process of inflation of dilator balloon 113 is performed in a gentle and gradual manner to slowly apply an increasing radial force to the inner walls of the ureter below the position of arrestment of stone 201. This application of radial force is of a magnitude and duration to distend the uretal inner walls sufficiently to induce a stress relaxation state therein as described in the section entitled "Background of the Invention." Correspondingly, the spacial area in the ureter below the stone. Balloon 113 is inflated until the minimum lateral diameter of the dilated spacial area is greater than the maximum diameter of stone 201. This requisite inflation is readily visualized and determined by the attending physician via the image intensifier screen.

When requisite inflation has occurred and the aforementioned stress relaxation state has been induced, dilator balloon 113 is deflated. Dilator catheter 101 is then withdrawn downwards until balloon 113 is in next non-dilated area of the ureter. Dilator balloon 13 is then again gradually inflated in the manner previously described.

With the spacial area below the stone distended, dislodger catheter 101 and dislodger balloon 107 are manipulated, by lated, by previously described strings 110, to dislodge the arrested stone 201 and move it downward into the dilated spacial area. It is advantageous, for manipulation purposes, to attach the pair of strings 110 to dislodger catheter 101 and balloon 107 in a manner such that the strings remain substantially equidistant from the walls 103 of catheter 101. The process of distending the inner ureteral walls to a stress relaxation state below the stone by dilator balloon 113, deflating balloon 113, and moving the stone 201 to the dilated spacial area of the ureter is repeated until stone 201 passes through the ureter and into the patient's bladder.

When stone 201 is within the bladder, it can easily be retrieved by the attending physician.

A stone extractor of the type depicted as extractor apparatus 100 and described herein in accordance with the invention has several advantages over prior art stone extraction systems. The absence of metal wires on the exterior of the apparatus which can accidentally protrude into ureteral walls provides a substantial probability of trauma occurring to the ureter during the previously described extraction procedure. Further, there is no chance of broken metal or metal being accidentally caught within the ureter which is unable to be withdrawn without major surgery. Additionally, relatively large sized stones can be withdrawn by utilization of an extractor in accordance with the invention, provided that the attending physician has the patience and skill to gradually dilate the ureter before attempting to manipulate the stone into the dilated area. Further, the utilization of an inflatable means such as a balloon which can be gradually inflated is physiologically advantageous for distending the ureteral walls and dilating the ureter. Conversely, any means of dilation which utilizes a sudden or rapid ureteral wall distension can cause folds of mucosa to be produced ahead of the stone. The mucosal folds can be damaged if an extraction force is then applied to the stone.

The principles of the invention are not limited to a stone extractor completely equivalent to the extractor 100 described herein. It will be apparent to those skilled in the medical arts that modifications and variations of the above-described illustrative embodiment of the invention may be effected without departing from the spirit and scope of the novel concepts of the invention.

The embodiments of the invention in which an exclusive property or privilege is claimed are defined as follows:

1. A stone extractor for extracting a ureteral stone arrested within any of various sections of a ureter of a patient wherein said various sections include ureteral sections above the lower third sectional area of said ureter; said stone extractor comprising:
   first inflatable means for gradually applying an increasing outward radial force to inner walls of said ureter wherein said inner walls are distended in response to said radial force in a manner such that a stress relaxation state is induced therein;
   first catheter means connected to said first inflatable means and adapted to position said first inflatable means below the position of arrestment of said ureteral stone;
   second inflatable means for applying a downward force to said ureteral stone to achieve dislodgment of said stone from said inner walls of said ureter;
   second catheter means connected to said second inflatable means for positioning said second inflatable means above the position of arrestment of said ureteral stone; and
   said second catheter means is adapted to adjust the position of said second inflatable means relative to said first inflatable means and is manually manipulable to move said ureteral stone into a spacial area of said ureter distended by said first inflatable means.

2. A stone extractor in accordance with claim 1 characterized in that said second inflatable means comprises a dislodger balloon connected to and arranged eccentrically about said second catheter means.

3. A stone extractor in accordance with claim 1 or 2 characterized in that said first catheter means comprises a dilator catheter manually extendable into said ureter and connected to said first inflatable means for positioning said first inflatable means below said ureteral stone.

4. A stone extractor in accordance with claim 3 characterized in that said first inflatable means comprises a dilator balloon connected to and arranged concentrically about said dilator catheter; and
   said stone extractor further comprises means for inflating said dilator balloon through said dilator catheter subsequent to insertion of said dilator catheter into said ureter, wherein said means for inflating said dilator balloon is manually operable external to said ureter.

5. A stone extractor in accordance with claims 1 or 2 characterized in that said stone extractor further comprises means connected to said second catheter means for externally manipulating said second inflatable means to move said uretal stone into said spacial area of said inner walls of said ureter distended by said first inflatable means.

6. A stone extractor in accordance with claim 5 characterized in that said means for externally manipulable said second inflatable means comprises a pair of strings connected to said second catheter means.

7. A stone extractor in accordance with claims 1 or 2 characterized in that said first catheter means comprises a dilator catheter having a diameter in the range of 7 to 8 F and comprising a dislodger lumen having openings at proximal and distal ends, and a relatively smaller inflating lumen having openings (115, 116) at proximal and distal ends;
   said first inflatable means comprises a dilator balloon having a cylindrical shape and arranged concentrically about said first lumen of said dilator catheter at said proximal end, said dilator balloon inflatable by injection of material through said opening of said second lumen at the distal end and through said proximal opening of said second lumen; and
   said dilator balloon having a volumetric capacity in the range of 9 to 11 cubic centimeters.

8. A stone extractor apparatus in accordance with claim 7 characterized in that said second catheter means comprises:
   a dislodger catheter having a diameter in the range of 3 to 4 F and comprising a lumen having an opening (108) at its proximal end and an opening (109) at its distal end;
   a dislodger balloon connected to said dislodger catheter and arranged eccentrically about said lumen of said dislodger catheter, said dislodger balloon inflatable by injection of material through said openings (109) 108) of said lumen of said dislodger catheter;
   said dislodger balloon having a volmetric capacity in the range of 1 to 3 cubic centimeters; and
   said dislodger catheter is manually insertable through and beyond said first lumen of said dilator catheter.

9. A stone extractor in accordance with claim 1 characterized in that said second inflatable means is adapted to prohibit extensive migration of said ureteral stone toward a kidney of said patient.

10. A stone extractor in accordance with claim 1 characterized in that said second catheter means comprises a dislodger catheter manually extendable into said ureter and connected to said second inflatable means for positioning said second inflatable means above said ureteral stone.

11. A stone extractor in accordance with claim 10 characterized in that said dislodger catheter terminates in a tapered end comprising a flexible material having wire means therein to provide rigidity for insertion of said dislodger catheter into said ureter.

12. A stone extractor in accordance with claim 10 characterized in that said first catheter means comprises a dilator catheter manually extendable into said ureter and connected to said first inflatable means for positioning said first inflatable means below said ureteral stone; and said dislodger catheter is manually extendable through and beyond said dilator catheter.

13. A stone extractor in accordance with claim 12 characterized in that said stone extractor further comprises means selectively extendable into said dislodger catheter for effecting substantial rigidity of said stone extractor during insertion of said dislodger catheter and said dilator catheter into said ureter.

14. A stone extractor in accordance with claim 13 characterized in that said means for effecting rigidity comprises a metal stylet having a diameter smaller than the diameter of said dislodger catheter.

15. A stone extractor in accordance with claim 10 characterized in that said second inflatable means comprises a dislodger balloon connected to and arranged eccentrically about said dislodger catheter; and said stone extractor further comprises means for inflating said dislodger balloon through said dislodger catheter subsequent to insertion of said dislodger catheter into said ureter.

16. A method for extracting a stone arrested in a ureter of a patient above the pelvi-ureteric junction, said method comprising the steps of:

(a) applying a gradually increasing outward radial force to a first portion of inner walls of said ureter immediately below the position of said stone within said ureter and sufficient to induce a stress relaxation state of said inner walls to the extent that the diameter of a spacial area at said first portion of said inner walls is larger than the maximum diameter of said stone;

(b) ceasing application of said radial force at said first portion;

(c) applying a downward force from a position above the position of said stone sufficient to dislodge said stone from said inner walls while said first portion of said inner walls are in said stress relaxation state;

(d) manipulating said stone downward into said spacial area at said first portion of said inner walls of said ureter; and (e) sequentially repeating steps (a) through (d) at successive lower portions of said inner walls of said ureter until said stone passes into the bladder area of said patient.

17. The method in accordance with claim 16 characterized in that said method further comprises prohibiting, migration of said stone toward a kidney of said patient prior to step (a).

* * * * *